United States Patent
Nakashima et al.

(10) Patent No.: US 9,278,114 B2
(45) Date of Patent: Mar. 8, 2016

(54) BRAIN TISSUE REGENERATION METHOD

(71) Applicant: National Center for Geriatrics and Gerontology, Aichi (JP)

(72) Inventors: Misako Nakashima, Obu (JP); Masahiko Sugiyama, Obu (JP)

(73) Assignee: National Center for Geriatrics and Gerontology, Aichi (JP)

(*) Notice: Subject to any disclaimer, the term of this patent is extended or adjusted under 35 U.S.C. 154(b) by 133 days.

(21) Appl. No.: 13/971,037

(22) Filed: Aug. 20, 2013

(65) Prior Publication Data

US 2013/0330303 A1 Dec. 12, 2013

Related U.S. Application Data

(62) Division of application No. 13/059,710, filed as application No. PCT/JP2009/065024 on Aug. 21, 2009, now abandoned.

(30) Foreign Application Priority Data

Aug. 22, 2008 (JP) ................................ 2008-214205

(51) Int. Cl.
*A61K 35/32* (2015.01)
*A61L 27/38* (2006.01)

(52) U.S. Cl.
CPC ............. *A61K 35/32* (2013.01); *A61L 27/3834* (2013.01); *A61L 27/3878* (2013.01)

(58) Field of Classification Search
None
See application file for complete search history.

(56) References Cited

U.S. PATENT DOCUMENTS

2007/0274958 A1* 11/2007 Shi et al. ...................... 424/93.7

FOREIGN PATENT DOCUMENTS

| JP | 2007-014780 | 1/2007 |
|----|-------------|--------|
| JP | 2007-130026 | 5/2007 |

OTHER PUBLICATIONS

Arthur et al, Stem Cells, 2008, vol. 26, No. 7, pp. 1787-1795 (e-pub May 22, 2008).*
Gronthos et al, PNAS, 2000, vol. 97, No. 25, pp. 13625-13630.*
Gandia et al. "Human Dental Pulp Stem Cells Improve Left Ventricular Function, Induce Angiogenesis, and Reduce Infarct Size in Rats with Acute Myocardial Infarction", *Stem Cells* 26(3):638-345 (2008).
Final Office Action corresponding to Japanese Application No. 2010-525733 issued Mar. 3, 2014.
Agata et al. "Effect of ischemic culture conditions on the survival and differentiation of porcine dental pulp-derived cells", *Differentiation* 76:981-993 (2008).
Iohara et al. "Side Population Cells Isolated from Porcine Dental Pulp Tissue with Self-Renewal and Multipotency for Dentinogenesis, Chondrogenesis, Adipogenesis, and Neurogenesis", *Stem Cells* 24:2493-2503 (2006).
Sugiyama et al. "Shizui Yurai CD31-SP Saibo no Nokyoketsu Shikan Chiryo ni Taisuru Yukosei no Kento", *Regenerative Medicine* 7:255 (2008).
Sugiyama et al. "Shizui CD31 Insei SP Saibo no Shizui Oyobi No Soshiki ni Okeru Shinkei Kekkan Saisei ni Taisuru Koka no Kento", *Nippon Shika Hozon Gakkai Gakujutsu Taikai Program Oyobi Koen Shorokushu* 128:49 (2008).
International Search Report corresponding to International Application No. PCT/JP2009/065024 mailed Oct. 6, 2009.

* cited by examiner

*Primary Examiner* — Allison Fox
(74) *Attorney, Agent, or Firm* — Myers Bigel Sibley, P.A.

(57) ABSTRACT

A material for treatment of cerebral infarction ameliorates angiopathy at a cerebral infarction region and improves brain function. The material for treatment of cerebral infarction according to the present invention comprises a dental pulp stem cell including at least one of a CD105-positive cell, an SP cell, a CD24-positive cell, a CD271-positive cell, and a CD150-positive cell. The material for treatment of cerebral infarction according to the present invention may contain a secretory protein of the dental pulp stem cell. Transplanted dental pulp stem cells do not directly differentiate into neural progenitor cells or neural cells and indirectly participate in the promotion of differentiation to restore and cure a cerebral infarction region such that the region becomes normal.

15 Claims, 15 Drawing Sheets

10μm

10μm

10μm

10μm

1: normal rat brain
2: normal porcine brain
3: stroke+, Cell+
4: stroke-, Cell+

500μm

500μm control  BMP2

*Dspp*

*enamelysin*

*β-actin*

100 μm

50 μm

100 μm

50 μm

BRAIN TISSUE REGENERATION METHOD

RELATED APPLICATIONS

This application is divisional application of U.S. application Ser. No. 13/059,710, filed Mar. 14, 2011, which is a 35 U.S.C. §371 national stage application of PCT Application No. PCT/JP2009/065024, filed on Aug. 21, 2009, which claims priority from Japanese Application No. 2008-214205 filed Aug. 22, 2008, the contents of each of which are incorporated herein by reference in their entireties.

STATEMENT REGARDING ELECTRONIC FILING OF A SEQUENCE LISTING

A Sequence Listing in ASCII text format, submitted under 37 C.F.R. §1.821, entitled 5576-231TSDV_ST25.txt, 5,167 bytes in size, generated on Aug. 19, 2013 and filed via EFS-Web, is provided in lieu of a paper copy. This Sequence Listing is hereby incorporated by reference into the specification for its disclosures.

FIELD AND BACKGROUND OF THE INVENTION

The present invention relates to a material for treatment of cerebral infarction and to a brain tissue regeneration method using the material for treatment of cerebral infarction.

Cerebral angiopathy is the second leading cause of death in Japan and is responsible for the greatest cause of being bedridden, while not causing death. Therefore, the aging society is in urgent need of development of therapy appropriate for cerebral angiopathy.

Among cerebral angiopathies, ischemic cerebrovascular disease such as cerebral infarction or cerebral thrombosis occurs with the highest frequency. Mortality due to cerebral infarction is greater than the total mortality due to myocardial infarction and ischemic heart disease.

If the cause of paralysis is cerebral infarction, current treatment is thought to be effective within 3 hours after development, at present.

In addition, rtPa (recombinant tissue plasminogen activator) intravenous drip treatment can be expected to have recanalization effect and offers functional recovery of up to approximately 30% of damaged brain function.

However, the rtPa intravenous drip treatment has the disadvantage that it is used in only approximately 2% of cases due to adverse reactions of intracerebral hemorrhage.

Moreover, thrombolytic therapy using catheters has been approved by the Ministry of Health, Labour and Welfare of Japan. However, under the present circumstances, no drug used in this therapy is covered by national health insurance.

In the adult brain, the region where new neurons are produced is thought to be located in the lateral subventricular zone and in the granular cell layers of the hippocampal dentate gyrus.

In addition, new neurons formed after cerebral infarction are derived from the lateral subventricular zone. These neurons migrate to the parenchyma of the corpus striatum to form chain-like cell aggregates, which in turn differentiate into nerves of the corpus striatum and form synapses.

Moreover, blood vessels are thought to participate in the control of neural progenitor cell differentiation and influence induced nerve regeneration in the corpus striatum.

The development of therapy based on regenerative medicine has been pursued for cerebral infarction, and preclinical experiments using rat or mouse models of cerebral infarction have been practiced.

Stem cells derived from bone marrow, peripheral blood, adipose, or umbilical cord blood, or the like are used as transplanted cells. Embryonic neural stem cells or ES cells, or the like are also used. These cells are injected into the brain or veins.

As a result, these cells may directly differentiate into nerves, thereby decreasing cerebral infarction regions, restoring brain function, or may promote angiogenesis in peri-infarct areas.

For example, Japanese Patent Laid-Open No. 2007-130026 discloses a method for efficiently inducing in vitro or in vivo the growth of neural stem cells that are important for, for example, the treatment of nerve injury sites caused by cerebral infarction.

In addition, for example, Japanese Patent Laid-Open No. 2007-014780 discloses pharmaceuticals for cerebral infarction regions comprising mesenchymal stem cells and IGF-1 in combination.

However, these techniques have a difficulty in offering efficient functional recovery in cerebral infarction regions. Thus, an effective approach for ameliorating angiopathy at a cerebral infarction region and improving brain function has been demanded.

SUMMARY OF THE INVENTION

The present invention has been completed in consideration of the problems described above, and an object of the present invention is to provide a material for treatment of cerebral infarction that effectively ameliorates angiopathy at a cerebral infarction region and improves brain function, and to provide a brain tissue regeneration method using the material for treatment of cerebral infarction.

To attain the object, a material for treatment of cerebral infarction according to the first aspect of this invention includes at least one of: a dental pulp stem cell comprising at least one of a CD105-positive cell, a SP cell, a CD24-positive cell, a CD271-positive cell, and a CD150-positive cell; and secretory proteins of the dental pulp stem cells.

It is preferred that the SP cell be CD31-negative, CD105-positive, CD24-positive, CD271-positive, or CD150-positive.

It is preferred that the dental pulp stem cell express some factors including at least one of a cell migration factors, cell growth factors, angiogenic factors, and neurotrophic factors in a peri-infarct area of the brain.

It is preferred that the cell migration factors are at least one of SDF1, GCSF, MMP3, Slit, and GMCSF.

It is preferred that the neurotrophic factors are at least one of VEGF, NGF, GDNF, BDNF, LIF, MYC, Neurotrophine 3, TP53, and BAX.

It is preferred that the cell growth factors are at least one of bFGF and PDGF.

It is preferred that the angiogenic factors are at least one of PGF, CXCL1, CXCL2, CXCL3, CXCL5, CXCL10, ANPEP, NRP1, TGFβ, ECGF1, ID1, and CSF3.

It is preferred that the dental pulp stem cells have a concentration of $1 \times 10^5$ cells/μl to $1 \times 10^7$ cells/μl.

It is preferred that the dental pulp stem cells are stem cells derived from a permanent tooth or a deciduous tooth.

Moreover, to attain the object, a brain tissue regeneration method according to the second aspect of this invention includes injecting at least one of: a dental pulp stem cell including at least one of a CD105-positive cell, a SP cell, a CD24-positive cell, a CD271-positive cell, and a CD150-positive cell; and secretory proteins of the dental pulp stem cells, into the brain striatum after cerebral infarction, thereby regenerating the central nervous tissue of the brain to recover brain function.

It is preferred that the SP cells are CD31-negative, CD105-positive, CD24-positive, CD271-positive, or CD150-positive.

It is preferred that the dental pulp stem cells express a factor including at least one of a cell migration factor, a cell growth factor, an angiogenic factor, and a neurotrophic factor in a peri-infarct area of the brain.

It is preferred that the dental pulp stem cell have a concentration of $1 \times 10^5$ cells/µl to $1 \times 10^7$ cells/µl.

It is preferred that the dental pulp stem cell are stem cells derived from a permanent tooth or a deciduous tooth.

A material for treatment of cerebral infarction and a brain tissue regeneration method according to the present invention are an unprecedented, original, and novel material for treatment of cerebral infarction and brain tissue regeneration method. The material for treatment of cerebral infarction and the brain tissue regeneration method according to the present invention effectively ameliorate angiopathy at a cerebral infarction region and improve brain function. As a result, the symptoms of cerebral disorder such as stroke can be improved effectively. Thus, they make a great contribution to saving lives in an aging society and offer immeasurable benefits.

DESCRIPTION OF THE EMBODIMENTS OF THE INVENTION

Figure 1A:
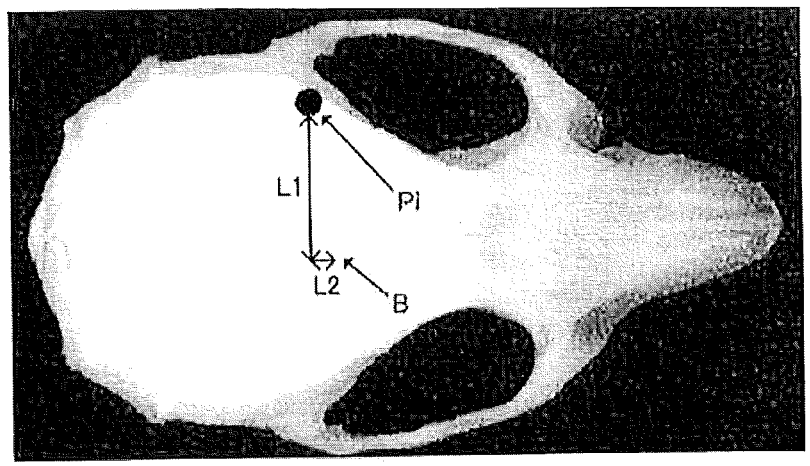
FIG. 1A illustrates cell transplantation to the brain striatum.

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

A material for treatment of cerebral infarction according to this embodiment contains dental pulp stem cells, secretory proteins of the dental pulp stem cells, or a mixture thereof.

The present inventors have found that the dental pulp stem cells or the secretory proteins of the dental pulp stem cell transplanted into a cerebral infarction region indirectly contributes to the promotion of differentiation of neural progenitor cells and neural stem cells on the periphery of the cerebral infarction region. Based on this previously unseen, original, and novel finding, the present invention has been completed.

The dental pulp stem cell is more advantageous than other stem cells such as bone marrow stem cells and adipose stem cells in that it restores cerebral infarction region.

Dental pulp tissues are rich in stem cells, and it is easier to fractionate them than, for example, bone marrow tissues and adipose tissues. For example, SP cells are found in porcine dental pulp tissue:porcine bone marrow tissue:porcine adipose tissue=3%:0.3%:1.3%. Moreover, VEGFR2-positive cells are found in porcine dental pulp tissue:porcine bone marrow tissue:porcine adipose tissue=87%:43%:46%.

Moreover, the dental pulp stem cell is advantageous in that it has a higher growth rate than that of, for example, bone marrow stem cells. For example, porcine dental pulp stem cells require a time for SP cell subculture that is about twice shorter than that of porcine bone marrow stem cells.

Moreover, the dental pulp stem cell is advantageous in that it expresses larger amounts of blood vessel-inducing factors such as G-CSF, GM-CSF, MMP3, and VEGF than those of, for example, bone marrow stem cells and adipose stem cells. For example, canine dental pulp stem cells express G-CSF, GM-CSF, and VEGF in amounts infinite times, 3.8 times, and 3.6 times, respectively, greater than those of canine adipose stem cells in CD105-positive real-time RT-PCR.

Moreover, the dental pulp stem cells more easily form a tube-like structure on matrigel in vitro than, for example, bone marrow stem cells, aortic stem cells, and adipose stem cells.

Moreover, the dental pulp stem cells are advantageous in that they more significantly ameliorate blood flow and more significantly promote angiogenesis than, for example, bone marrow stem cells and adipose stem cells. For example, when transplanted into mice with lower limb ischemia, porcine dental pulp stem cells more significantly induce angiogenesis than porcine bone marrow stem cells and porcine adipose stem cells.

Moreover, the dental pulp stem cells are advantageous in that they express larger amounts of neural factors such as BDNF, NPY, TGFβ1, and TGFβ3 than those of, for example, bone marrow stem cells and adipose stem cells. For example, the dental pulp stem cells express BDNF in an amount 19 times greater than that of bone marrow stem cells and 2 times greater than that of adipose stem cells. Moreover, the dental pulp stem cells express NPY in an amount 7 times greater than that of bone marrow stem cells and 9 times greater than that of adipose stem cells.

Moreover, bone marrow stem cells are disadvantageous in that bone marrow puncture is highly burdensome and the number of stem cells decreases with age. Adipose stem cells have poor collection efficiency due to large collection amounts required for obtaining the stem cells. Umbilical cord blood stem cells are disadvantageous in that they are too susceptible to the time required from parturition to cell collection and the amount of umbilical cord blood to stably collect the stem cells, in addition to the low frequency of the stem cells present. ES cells present a safety problem in addition to ethical and social problems. Embryonic-derived neural stem cells also present a safety problem in addition to ethical and social problems.

In contrast, dental pulp stem cells are more advantageous than other stem cells in that: the collection of wisdom teeth and deciduous teeth has low invasiveness to the human body; it presents a few ethical problems because it is medical waste; the timing of obtainment is not limited; its collection requires neither special tools nor techniques; and it has high growth potential and multipotency, as shown herein.

The dental pulp stem cell can be cryopreserved with its traits maintained. It has much higher immunosuppressive activity that suppresses the alloreactivity of T cells, than that of bone marrow stem cells.

The dental pulp stem cell includes at least one of a CD105-positive cell, a SP cell, a CD31-negative and CD146-negative cell, a CD24-positive cell, a CD271-positive cell, and a CD150-positive cell.

The SP cell refers to an undifferentiated cell that was discovered by Goodell et al. (J. Exp. Med. vol. 183, 1996). This cell population appears in flow cytometry analysis at a position (lower left, dark fluorescent region, i.e., "weakly Hoechst Blue-positive and weakly Hoechst Red-positive") different from that of usual cells (cells other than undifferentiated cells) emitting fluorescence at 405 nm and 600 nm on cytogram, when the SP cell is allowed to incorporate therein a fluorescent dye Hoechst 33342 and then excited with UV. The SP cells are CD31-negative, CD105-positive, CD31-negative and CD146-negative, CD24-positive, CD271-positive, or CD150-positive.

The dental pulp stem cells express a cell migration factor, a cell growth factor, an angiogenic factor, or a neurotrophic factor in a peri-infarct area of the brain.

The cell migration factors are at least one of SDF1, GCSF, MMP3, Slit, and GMCSF.

The neurotrophic factors are at least one of VEGF, NGF, GDNF, BDNF, LIF, MYC, Neurotrophine 3, TP53, and BAX.

The cell growth factors are at least one of bFGF and PDGF.

The angiogenic factors are at least one of PGF, CXCL1, CXCL2, CXCL3, CXCL5, CXCL10, ANPEP, NRP1, TGFβ, ECGF1, ID1, and CSF3.

The concentration of the dental pulp stem cells contained in the material for treatment of cerebral infarction is not particularly limited and is preferably, for example, $1 \times 10^5$ cells/µl to $1 \times 10^7$ cells/µl. This is because: dental pulp stem cells having a concentration less than $1 \times 10^5$ cells/µl may possibly make a reduced contribution to the promotion of differentiation of neural progenitor cells and neural cells; and, on the other hand, dental pulp stem cells having a concentration greater than $1 \times 10^7$ cells/µl may possibly be transplanted in unnecessary amounts into a cerebral infarction region.

The dental pulp stem cell may be a cell extracted from a target animal itself (autologous cell) undergoing treatment for improving brain function or may be a cell extracted from an animal other than the target animal (heterologous or xenologous cell) undergoing treatment for improving brain function.

Dental pulp stem cells derived from a permanent tooth or a deciduous tooth can be used. In particular, human deciduous tooth-derived dental pulp cells contain CD105$^+$ cells in an amount as great as approximately 30% (human permanent tooth-derived CD31$^-$ SP cells contain approximately 20% CD105$^+$ cells). The deciduous tooth-derived dental pulp stem cells or dental pulp cells exhibit the effects of inducing blood vessels in vitro, ameliorating blood flow at lower limb ischemia, and promoting angiogenesis, as with permanent tooth-derived dental pulp cells. Moreover, the deciduous tooth-derived dental pulp cells contain 0.5% of CD150$^+$ cells, which are higher than 0.2% in the permanent tooth-derived CD31$^-$ SP cells. The deciduous tooth-derived dental pulp cells have higher effects of inducing blood vessels in vitro, ameliorating blood flow at lower limb ischemia, and promoting angiogenesis than those of permanent tooth-derived dental pulp cells.

The material for treatment of cerebral infarction according to this embodiment not only includes the dental pulp stem cell but may also include secretory proteins of the dental pulp stem cells.

In this context, the secretory protein is an extracellularly secreted protein. The secretory protein has a sequence called a secretory signal peptide at the N terminus.

A brain tissue regeneration method according to this embodiment includes injecting the material for treatment of cerebral infarction into the brain striatum after cerebral infarction, thereby regenerating a central nervous tissue of the brain to recover brain function.

The injection into the brain striatum is not particularly limited and can be performed, for example, by making a hole in a portion of parietal bone.

In this context, the cerebral infarction refers to brain tissue death attributed to deteriorated blood flow due to the clogging or narrowing of cerebral blood vessels.

The brain striatum is the subcortical structure of the telencephalon. The brain striatum is deeply involved in motor functions and decision-making functions, and the like, and is one of the main components of basal ganglia in the cerebrum.

The brain striatum may be neostriatum or ventral striatum. The neostriatum is also called dorsal striatum and is composed of the putamen and the caudate nucleus. The ventral striatum contains the nucleus accumbens and the olfactory tubercle, etc.

The material for treatment of cerebral infarction can be injected into the brain striatum, for example, within 24 hours after the development of cerebral infarction, without particular limitations.

Hereinafter, the present invention is described specifically by showing examples and the like. However, the present invention is not limited to the examples and the like.

EXAMPLES

Example 1

This Example shows nerve regeneration by porcine dental pulp tissue-derived CD31$^-$/CD146$^-$ SP transplantation into rats after cerebral infarction.

Middle cerebral artery occlusion was performed using SD (Sprague-Dawley) rats to prepare rat models of cerebral infarction.

Figure 1B:
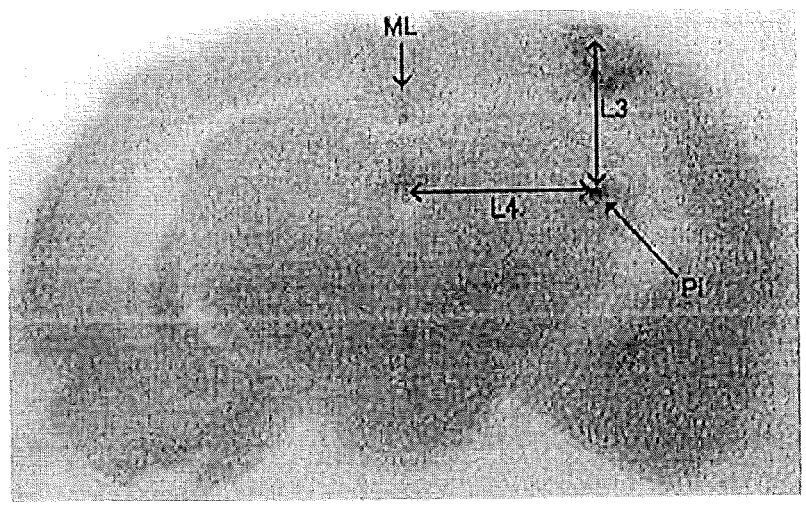
FIG. 1B is a macro image of a cross-section of the brain.

CD31-negative SP cells were fluorescently labeled with DiI and then transplanted 24 hours after cerebral infarction into an injection site Pi of the brain striatum in the brain tissues, as shown in FIGS. 1A and 1B. A PBS-injected control was used.

In FIG. 1A, B represents bregma, which is a point of intersection of the sagittal suture with the coronal suture of the cranium. L1 represents 6.0 mm, and L2 represents 1.0 mm.

FIG. 1B is a macro image of a coronal section. L3 represents 5.0 mm, and L4 represents 6.0 mm. ML represents a midline.

On day 21 after cell transplantation, perfusion fixation was performed, and frozen sections were prepared according to a routine method and immunostained with a neural progenitor cell marker, DCX, and neural markers, neurofilament and NeuN.

Figure 2A:
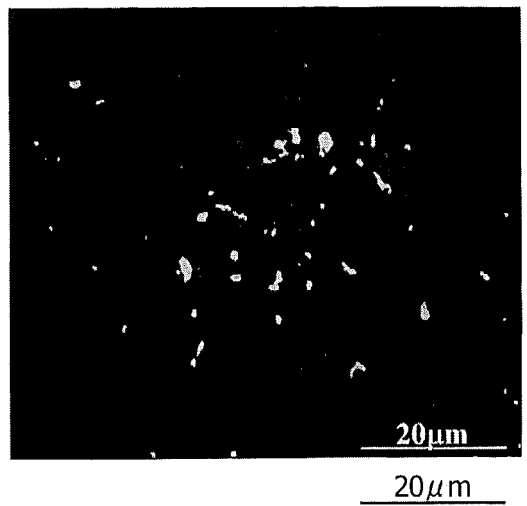
FIG. 2A is a confocal scanning laser microscopic image of a DCX-immunofluorescently stained frozen sections of a peri-infarct area of the brain on day 21 from the transplantation of porcine dental pulp tissue-derived CD31-negative SP cells 24 hours after cerebral infarction.
Figure 2B:
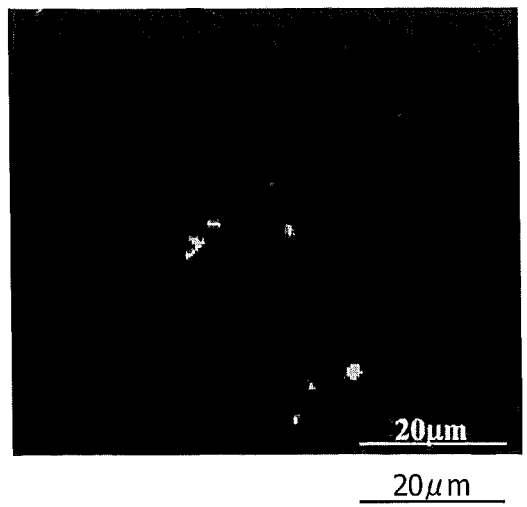
FIG. 2B is a confocal scanning laser microscopic image of a DCX-immunofluorescently stained frozen section of a normal brain region located on the contralateral side of the cerebral infarction region.
Figure 2C:
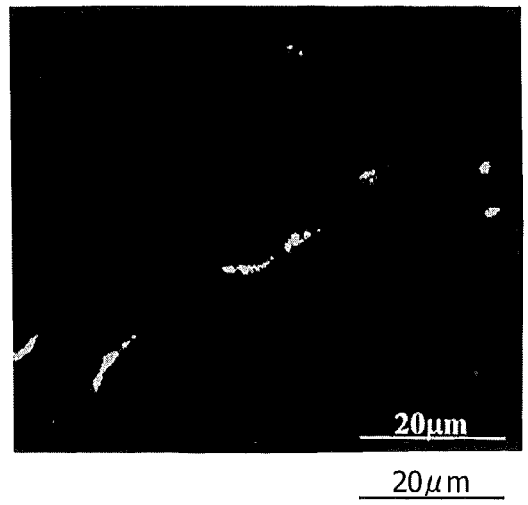
FIG. 2C is a confocal scanning laser microscopic image of a DCX-immunofluorescently stained non-cell-transplanted PBS control of a peri-infarct area of the brain.

FIG. 2A is a confocal scanning laser microscopic image of a DCX-immunofluorescently stained frozen section of a site transplanted with CD31-negative SP cells after cerebral infarction. FIG. 2B shows a DCX-immunostained section of a normal brain region located on the contralateral side of the cerebral infarction region. FIG. 2C shows a DCX-immunostained section of a control injected with PBS after cerebral infarction.

In these rat models of cerebral infarction, the infarction occurred in ¼ to ⅓ of the cerebral hemisphere after 1 month. According to the immunostaining (green) with the neural progenitor cell marker, DCX, the DiI-stained (red) transplanted cells accumulated on the periphery of the infraction region and were not confirmed to overlap with DCX-positive cells, while located in proximity to the DCX-positive cells. A few positive cells were observed on the contralateral side of the cerebral infarction region and on the periphery of the cerebral infarction region non-transplanted with CD31-negative SP cells.

Figure 3A:
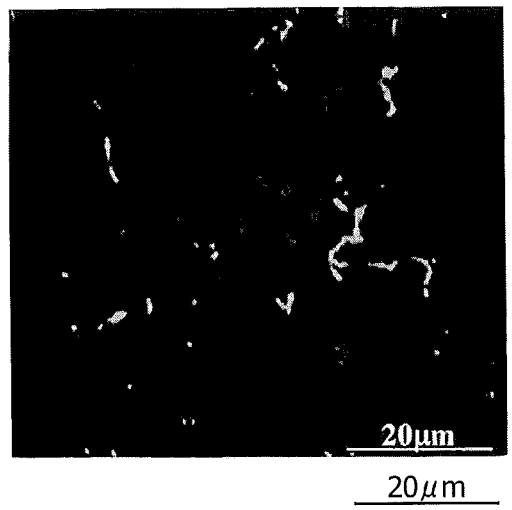
FIG. 3A is a confocal scanning laser microscopic image of a neurofilament-immunofluorescently stained frozen section of a peri-infarct area of the brain on day 21 from the transplantation of porcine dental pulp tissue-derived CD31-negative SP cells 24 hours after cerebral infarction.
Figure 3B:
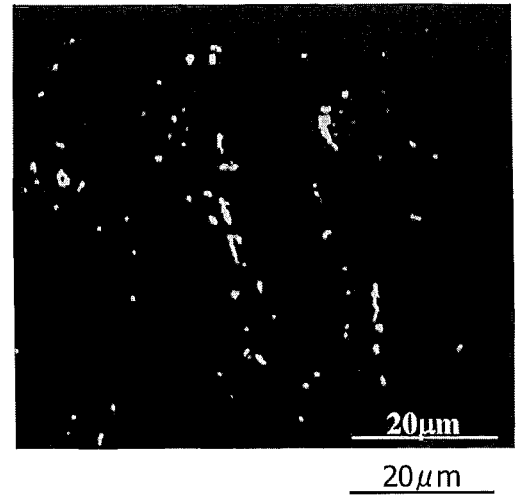
FIG. 3B is a confocal scanning laser microscopic image of a neurofilament-immunofluorescently stained frozen section of a normal brain region located on the contralateral side of the cerebral infarction region.
Figure 3C:
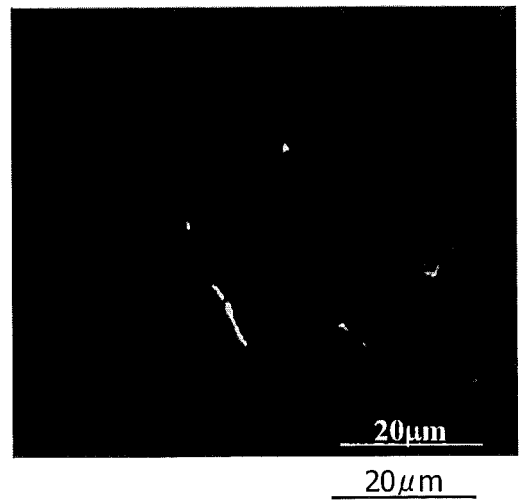
FIG. 3C is a confocal scanning laser microscopic image of a neurofilament-immunofluorescently stained non-cell-transplanted PBS control of a peri-infarct area of the brain.

Next, FIG. 3A is a confocal scanning laser microscopic image of a neurofilament-immunofluorescently stained frozen section of a site transplanted with CD31-negative SP cells after cerebral infarction. FIG. 3B shows a neurofilament-immunostained section of a normal brain region located on the contralateral side of the cerebral infarction region. FIG. 3C shows a neurofilament-immunostained section of a control injected with PBS after cerebral infarction.

According to the immunostaining with the neural cell marker neurofilament, its positive cells were not confirmed to overlap with cells accumulating in the peri-infarct area of the brain, while located in proximity to the cells. A very few neurofilament-positive cells were observed in the non-cell-transplanted peri-infarct area of the brain.

Figure 4A:
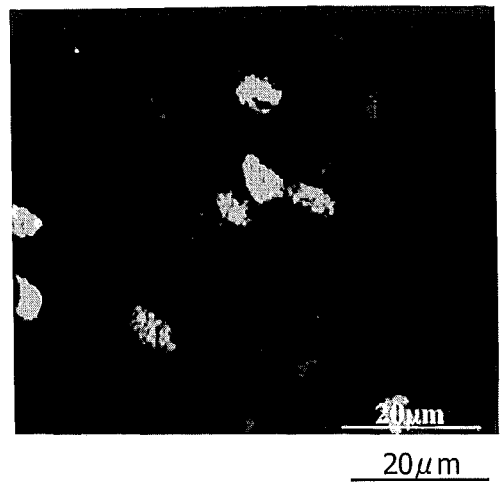
FIG. 4A is a confocal scanning laser microscopic image of a NeuN-immunofluorescently stained frozen section of a peri-infarct area of the brain on day 21 from the transplantation of porcine dental pulp tissue-derived CD31-negative SP cells 24 hours after cerebral infarction.
Figure 4B:
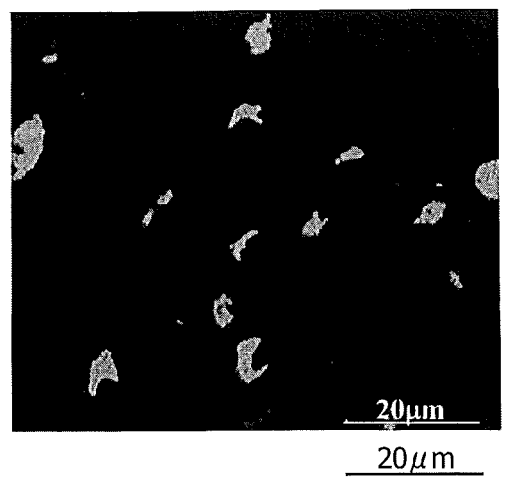
FIG. 4B is a confocal scanning laser microscopic image of a NeuN-immunofluorescently stained frozen section of a normal brain region located on the contralateral side of the cerebral infarction region.
Figure 4C:
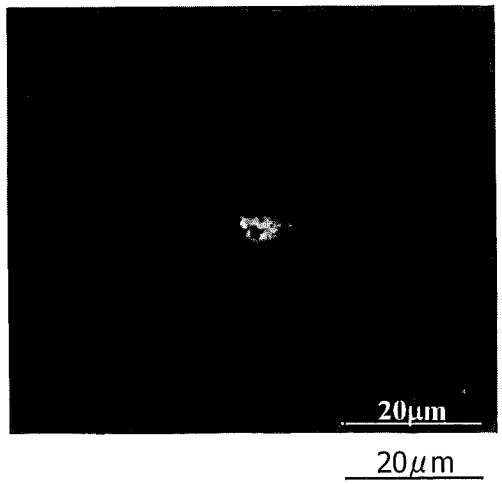
FIG. 4C is a confocal scanning laser microscopic image of a NeuN-immunofluorescently stained non-cell-transplanted PBS control of a peri-infarct area of the brain.

Next, FIG. 4A is a confocal scanning laser microscopic image of a NeuN-immunofluorescently stained frozen section of a site transplanted with CD31-negative SP cells after cerebral infarction. FIG. 4B shows a NeuN-immunostained section of a normal brain region located on the contralateral side of the cerebral infarction region. FIG. 4C shows a NeuN-immunostained section of a control injected with PBS after cerebral infarction.

Also in the NeuN immunostaining, its positive cells were not confirmed to overlap with cells accumulating in the peri-infarct area of the brain, while located in proximity to the cells, as with the neurofilament immunostaining. Moreover, only a few positive cells were observed in the non-cell-transplanted peri-infarct area of the brain. The NeuN staining is a method for staining proteins specific for the nuclei of neural cells. This method is used, for example, to distinguish between undifferentiated neural stem cells and differentiated neural cells.

It has previously been said that after cerebral infarction, lateral subventricular zone-derived neural progenitor cells and neural stem cells migrate to the parenchyma of the corpus striatum where they in turn differentiate into nerves and form synapses. Nevertheless, as is evident from the results of FIGS. 2A to 2C, 3A to 3C, and 4A to 4C, neural progenitor cells in the PBS-injected sample migrated to the corpus striatum due to cerebral infarction but were not confirmed to differentiate into the nerves, whereas no overlap with DCX-, neurofilament-, and NeuN-positive cells was seen in the cell-transplanted sample, suggesting that the transplanted cells do not directly differentiate into neural progenitor cells or neural cells and indirectly participate in the promotion of differentiation.

Next, a region (width: 6 mm) containing the entire cerebral infarction region was cut by 1.2 mm into 5 serial sections, which were then immunostained. Two typical regions of the periphery of the cerebral infarction region in which the migration of transplanted CD31-negative SP cells was seen were photographed (10 regions in total per sample) with a KEYENCE fluorescence microscope. The fluorescence densities of DCX and NeuN were measured using a Dynamic cell count, thereby statistically analyzing the densities of neural progenitor cells and neural cells.

Figure 5:
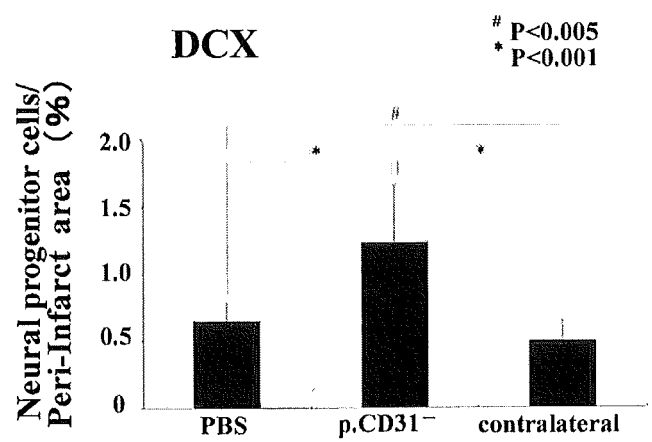
FIG. 5 shows results of statistically analyzing the density of neural progenitor cells on day 21 from the transplantation of porcine dental pulp tissue-derived CD31-negative SP cells 24 hours after cerebral infarction.

FIG. 5 shows results of statistically analyzing the density of neural progenitor cells in a sample transplanted with porcine dental pulp tissue-derived CD31$^-$/CD146$^-$ SP cells.

Figure 6:
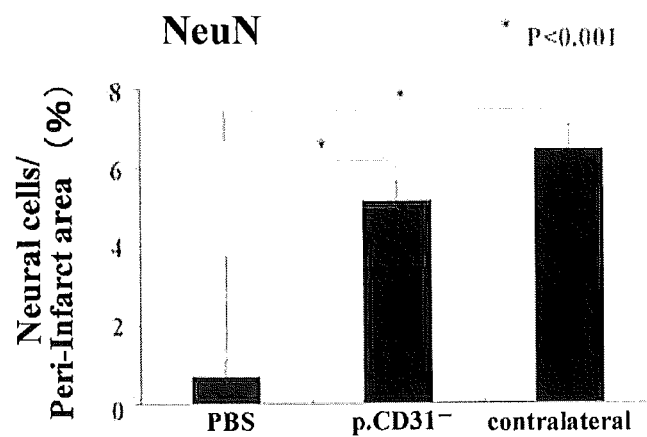
FIG. 6 shows results of statistically analyzing the density of neural cells on day 21 from the transplantation of porcine dental pulp tissue-derived CD31-negative SP cells 24 hours after cerebral infarction.

FIG. 6 shows results of statistically analyzing the density of neural cells in a sample transplanted with porcine dental pulp tissue-derived CD31$^-$/CD146$^-$ SP cells.

As shown in FIG. 5, neural progenitor cells on the periphery of the cerebral infarction region were increased by about 2 times compared with the PBS control, due to cell transplantation.

Moreover, as shown in FIG. 6, neural cells on the periphery of the cerebral infarction region were increased by about 8 times compared with the PBS control, due to cell transplantation.

These results suggest that the transplantation of CD31-negative SP cells into a cerebral infarction region results in migration of neural progenitor cells to a peri-infarct area of the brain, promotes growth, inhibits apoptosis, and promotes differentiation into neural cells.

Next, the expression of neurotrophic factors was examined by in situ hybridization.

Figure 7A:
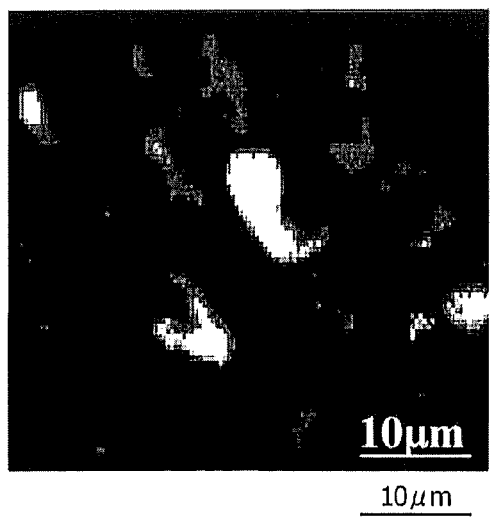
FIG. 7A shows the expression of VEGF mRNA at a cerebral infarction region transplanted with porcine dental pulp tissue-derived CD31-negative SP cells.
Figure 7B:
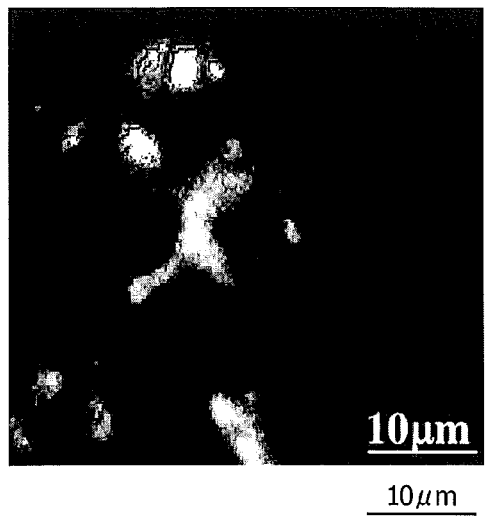
FIG. 7B shows the expression of GDNF mRNA at a cerebral infarction region transplanted with porcine dental pulp tissue-derived CD31-negative SP cells.
Figure 7C:
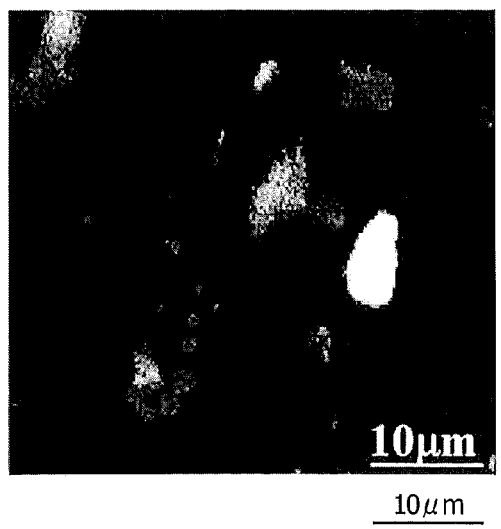
FIG. 7C shows the expression of BDNF mRNA at a cerebral infarction region transplanted with porcine dental pulp tissue-derived CD31-negative SP cells.
Figure 7D:
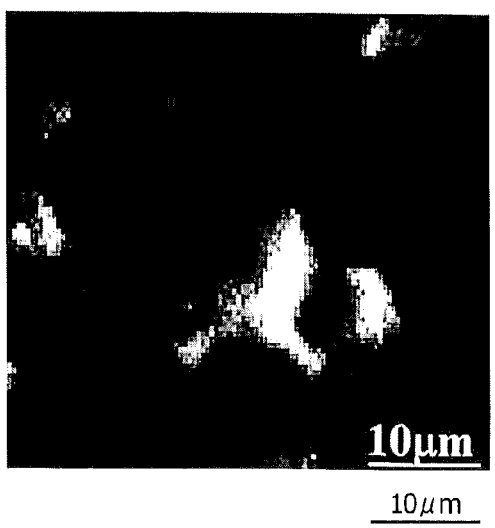
FIG. 7D shows the expression of NGF mRNA at a cerebral infarction region transplanted with porcine dental pulp tissue-derived CD31-negative SP cells.

FIG. 7A shows the expression of VEGF mRNA at the periphery of a cerebral infarction region. FIG. 7B shows the expression of GDNF mRNA in a peri-infarct area of the brain. FIG. 7C shows the expression of BDNF mRNA in a peri-infarct area of the brain. FIG. 7D shows the expression of NGF mRNA in a peri-infarct area of the brain. As shown in FIGS. 7A, 7B, 7C, and 7D, the transplanted cells strongly expressed VEGF mRNA, GDNF mRNA, BDNF mRNA, and NGF mRNA in the peri-infarct area of the brain.

Focusing particularly on VEGF, the expression of VEGF was examined by real-time RT-PCR using porcine-specific reactive primers:

```
(β-actin Forward:
                                   (SEQ ID NO: 1)
CTGGGGCCTAACGTTCTCAC, β-actin Reverse:
                                   (SEQ ID NO: 2)
GTCCTTTCTTCCCCGATGTT, VEGF Forward:
                                   (SEQ ID NO: 3)
ATGGCAGAAGGAGACCAGAA, VEGF Reverse:
                                   (SEQ ID NO: 4))
ATGGCGATGTTGAACTCCTC
```

The real-time RT-PCR employs a real-time PCR-specific apparatus integrally comprising a thermal cycler and a fluorescence spectrophotometer. The real-time RT-PCR analyzes the amount of PCR amplification by real-time monitoring. This technique requires no electrophoresis and is excellent in rapidity and quantitative performance.

Figure 8A:
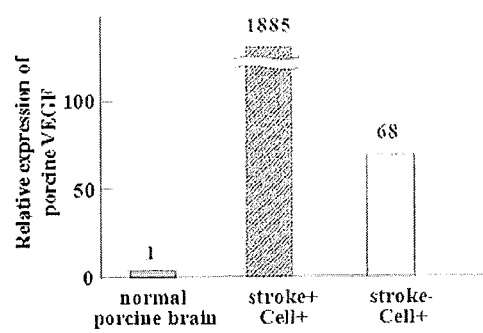
FIG. 8A shows an increase of the expression of VEGF mRNA caused by transplanted cells migrated to a peri-infarct area of the brain after the transplantation of porcine dental pulp tissue-derived CD31-negative SP cells.
Figure 8B:
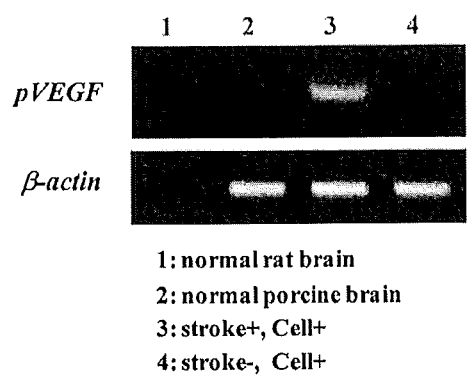
FIG. 8B shows results of real-time RT-PCR.

FIG. 8A shows the expression of VEGF in a peri-infarct area of the brain transplanted with porcine dental pulp tissue-derived CD31-negative SP cells. FIG. 8B shows results of measurement by real-time RT-PCR. As shown in FIGS. 8A and 8B, a 1000-fold or more rise in the expression of VEGF mRNA was seen in the peri-infarct area of the brain compared with the corresponding area of normal porcine brain, while an approximately 28-fold rise was seen therein compared with a cell-transplanted cerebral infarction-free region.

These results suggest that the transplantation of CD31-negative SP cells promotes the differentiation of neural progenitor cells and neural stem cells in a peri-infarct area of the brain, owing to neurotrophic factors including VEGF secreted from the transplanted cells.

Next, cultured neural progenitor cells (SHSY5Y human neuroblastomas) were used to examine a culture supernatant of CD31-negative SP cells for its migration, growth, and anti-apoptosis effects.

Figure 9:
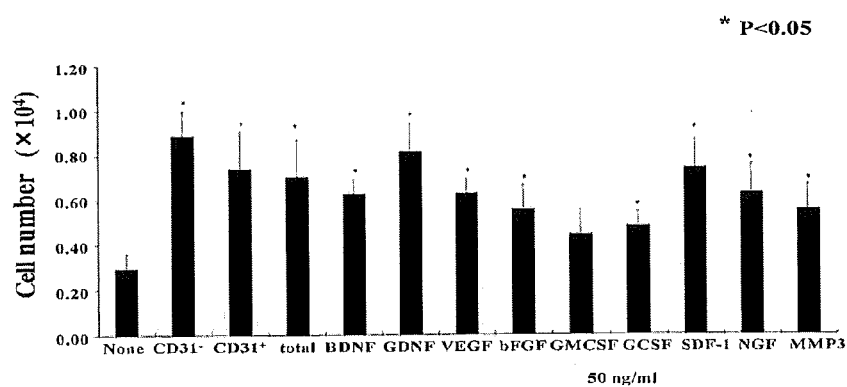
FIG. 9 shows the migratory effect of a culture conditioned medium of porcine dental pulp tissue-derived CD31-negative SP cells on neural progenitor cells.

FIG. 9 shows the migration effect of a culture supernatant of porcine dental pulp tissue-derived CD31-negative SP cells. As shown in FIG. 9, the culture supernatant of CD31-negative SP cells had excellent migration effect.

Figure 10:
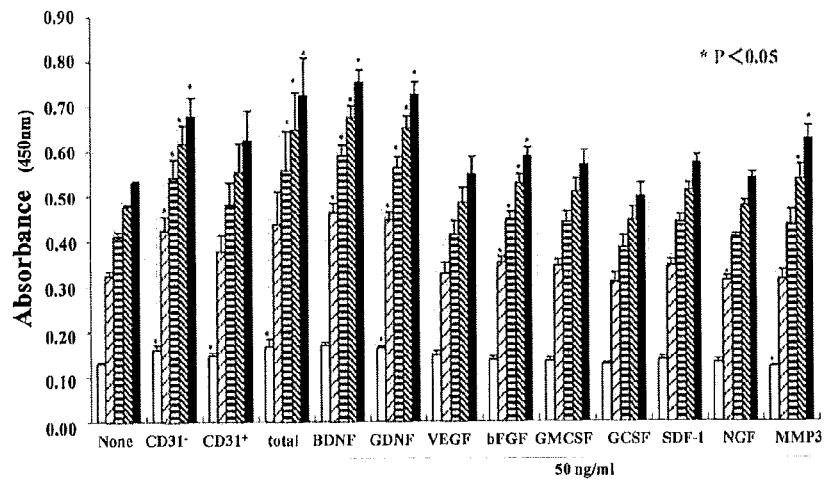
FIG. 10 shows the proliferative effect of a culture conditioned medium of porcine dental pulp tissue-derived CD31-negative SP cells on neural progenitor cells.

FIG. 10 shows the growth effect of a culture supernatant of porcine dental pulp tissue-derived CD31-negative SP cells. As shown in FIG. 10, the culture supernatant of CD31-negative SP cells had particularly superior growth effects.

The anti-apoptosis effect was determined by causing apoptosis with 400 nM staurosporine and measuring the proportions of necrotic cells and apoptotic cells by flow cytometry.

Figure 11:
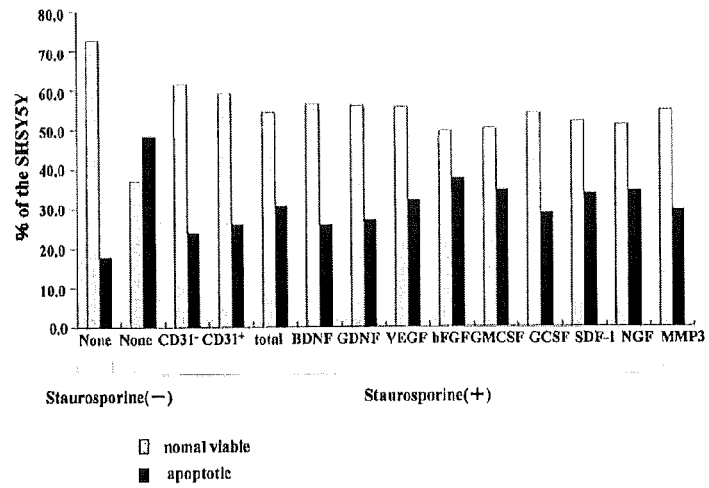
FIG. 11 shows the anti-apoptotic effect of a culture conditioned medium of porcine dental pulp tissue-derived CD31-negative SP cells on neural progenitor cells.

FIG. 11 shows the apoptosis inhibitory effect of a culture supernatant of porcine dental pulp tissue-derived CD31-negative SP cells. As shown in FIG. 11, the culture supernatant of CD31-negative SP cells had excellent apoptosis inhibitory effects.

Furthermore, porcine dental pulp tissue-derived CD31-negative SP cells were transplanted into rats with cerebral infarction. Then, their motor disability scores were determined over time to examine the recovery effect of cell transplantation on sensorimotor function.

The motor disability scores were calculated according to the following method:

1 . . . When lifted by lifting the tail, the rat is incapable of extending its upper limb on the paralyzed side (Score of 1).
2 . . . When a lower limb on the paralyzed side is pulled, the rat is incapable of pulling back the lower limb (Score of 1).
3 . . . When the body is tilted to the paralyzed side, the rat is inclined thereto (Score of 1).
4 . . . When forced to walk, the rat is incapable of walking (Score of 1).
5 . . . The rat is incapable of walking to escape within 10 seconds from a circle of 50 cm in diameter (Score of 1), within 20 seconds therefrom (Score of 2), and within 30 seconds therefrom (Score of 3).
6-1 . . . When upward resistance is applied to an upper limb on the paralyzed side, the rat is incapable of extending it (Score of 1).
6-2 . . . When forward resistance is applied to an upper limb on the paralyzed side, the rat is incapable of extending it (Score of 1).
6-3 . . . When lateral resistance is applied to an upper limb on the paralyzed side, the rat is incapable of extending it (Score of 1).

Figure 12:
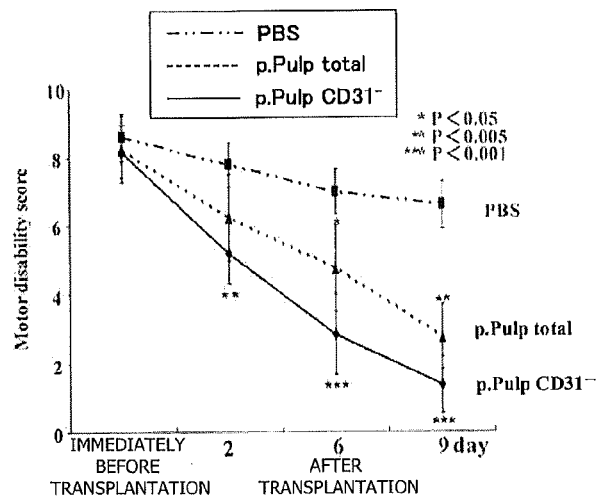
FIG. 12 shows results of determining over time and statistically analyzing the motor disability scores of rats with cerebral infarction into which porcine dental pulp tissue-derived CD31-negative SP cells were transplanted.

FIG. 12 shows results of determining over time and statistically analyzing the motor disability scores. The number of days is counted from cell transplantation. *$P<0.05$, $P<0.005$, *$P<0.001$.

As shown in FIG. 12, regarding the recovery effect of cell transplantation on sensorimotor function, almost complete recovery from motor disability was seen in the cell-transplanted rats on day 9, whereas little recovery was seen in the PBS control. When the motor disability scores were determined over time and statistically analyzed, the cell-transplanted group was confirmed to significantly recover motor function compared with the PBS-injected control group on day 6 or later. Moreover, porcine total dental pulp cells are cells in a state before fractionation of porcine dental pulp tissue-derived CD31-negative SP cells and include not only the porcine dental pulp tissue-derived CD31-negative SP cells but also the other cells. The group of rats in transplantation of the porcine total dental pulp cells showed better recovery from motor function than that in the PBS control, but less recovery than that in transplantation of the porcine dental pulp tissue-derived CD31-negative SP cells. These results demonstrated that superior recovery in motor function is obtained by the transplantation of only porcine dental pulp tissue-derived CD31-negative SP cells than by the transplantation of porcine total dental pulp cells.

Figure 13:
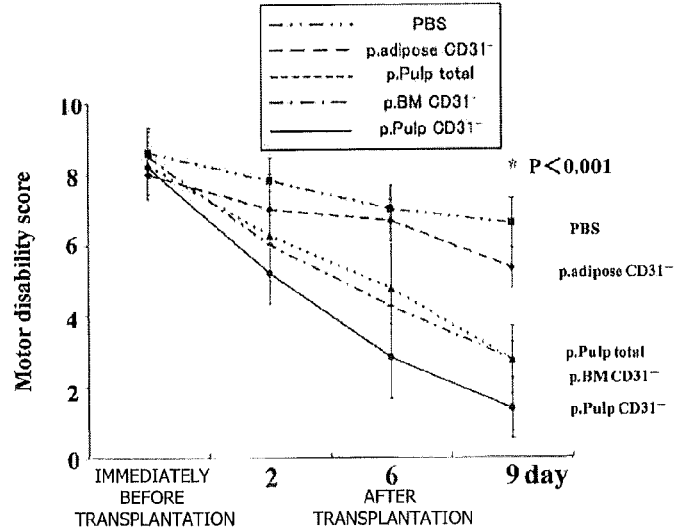
FIG. 13 shows results of determining over time and statistically analyzing the motor disability scores of rats with cerebral infarction into which porcine dental pulp tissue-derived CD31-negative SP cells, porcine bone marrow tissue-derived CD31-negative SP cells, and porcine adipose tissue-derived CD31-negative SP cells, were transplanted respectively.

The present inventors also compared porcine dental pulp tissue-derived CD31-negative SP cells, porcine total dental pulp cells, porcine bone marrow tissue-derived CD31-negative SP cells, and porcine adipose tissue-derived CD31-negative SP cells. Their respective motor disability scores were determined over time and statistically analyzed. The results shown in FIG. 13 demonstrated that the porcine dental pulp tissue-derived CD31-negative SP cells more significantly offer recovery in motor function than porcine bone marrow tissue-derived CD31-negative SP cells and porcine adipose tissue-derived CD31-negative SP cells. This suggested that dental pulp stem cells are more advantageous in functional improvement for cerebral infarction than bone marrow stem cells and adipose stem cells.

Example 2

Unlike Example 1, human dental pulp tissue-derived dental pulp cells are used in this Example. Table 1 shows the properties of human dental pulp tissue-derived CD31⁻ SP cells and porcine dental pulp tissue-derived CD31⁻ SP cells.

TABLE 1

| | Human CD31⁻ SP cell (%) | Human total dental pulp cell (%) | Porcine CD31⁻ SP cell (%) |
|---|---|---|---|
| CD31 | 0.00 | 0.06 | 0.00 |
| CD146 | 0.00 | 40.58 | 0.00 |
| CD24 | 0.10 | 23.87 | — |
| CD34 | 0.01 | 0.01 | 69.00 |
| CD44 | 92.50 | 91.60 | — |
| CD90 | 98.67 | 72.69 | 0.20 |
| CD105 | 21.23 | 4.35 | — |
| CD117 | 0.02 | 0.06 | 0.00 |
| CD133 | 0.01 | 0.47 | 0.00 |
| CD150 | 0.21 | 0.10 | 0.00 |
| CD271 | 0.03 | 0.01 | 94.00 |
| SSEA1 | 0.29 | 0.06 | — |

As shown in Table 1, the human dental pulp tissue-derived CD31⁻ SP cells highly expressed CD90 and CD150 compared with porcine dental pulp tissue-derived CD31⁻ SP cells, in flow cytometry. Moreover, the human dental pulp tissue-derived CD31⁻ SP cells highly expressed CD105 compared with human total dental pulp cells.

This Example shows nerve regeneration by the cell transplantation of human dental pulp tissue-derived CD31⁻/CD146⁻ SP cells and human dental pulp tissue-derived CD105⁺ cells into rats after cerebral infarction.

Table 2 shows the properties of human dental pulp tissue-derived CD31⁻/CD146⁻ SP cells and human dental pulp tissue-derived CD105⁺ cells.

Figure 14A:
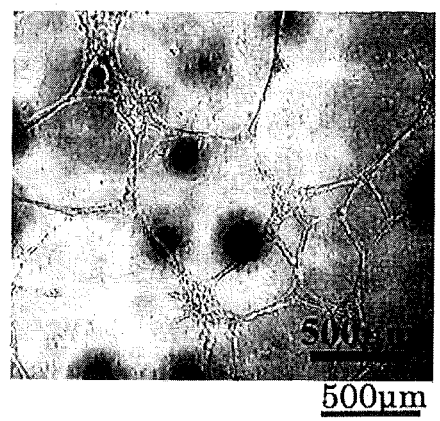
FIG. 14A shows the induction of differentiation of human dental pulp tissue-derived CD105$^+$ cells into blood vessels.
Figure 14B:
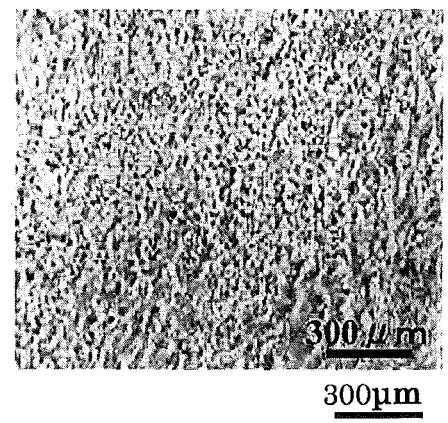
FIG. 14B shows the induction of differentiation of human dental pulp tissue-derived CD105$^+$ cells into adipose cells.
Figure 14C:
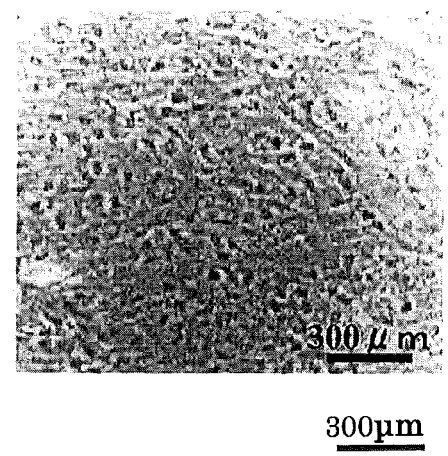
FIG. 14C shows results of a control without the induction of differentiation into adipose cells.
Figure 14D:
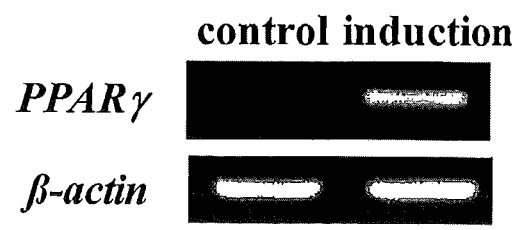
FIG. 14D shows results of determining the induction of differentiation into adipose cells by real-time RT-PCR.
Figure 14E:
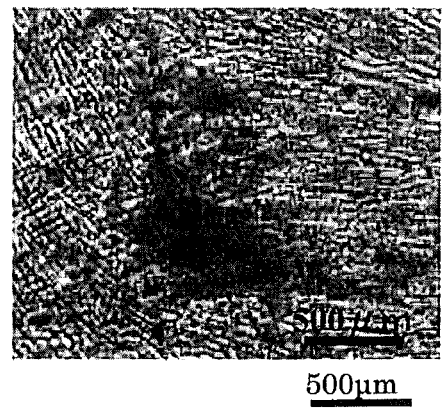
FIG. 14E shows the induction of differentiation of human dental pulp tissue-derived CD105$^+$ cells into odontoblasts.
Figure 14F:
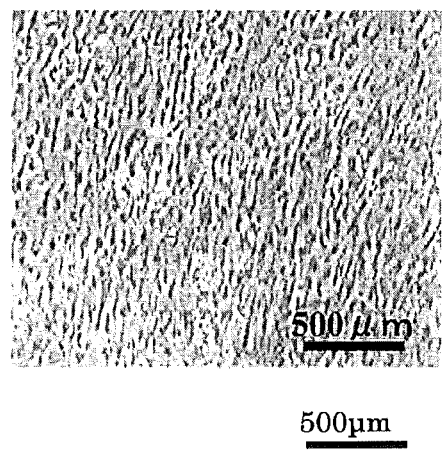
FIG. 14F shows results of a control without the induction of differentiation into odontoblasts.
Figure 14G:
FIG. 14G shows results of determining the induction of differentiation into odontoblasts by real-time RT-PCR.
Figure 14G:
Figure 14G:

Moreover, as shown in FIG. 14E, the human dental pulp tissue-derived CD105⁺ cells were induced to differentiate into odontoblasts. On the other hand, as shown in FIG. 14F, the induction of differentiation into odontoblasts was not seen in the PBS control. FIG. 14G shows results of measurement by real-time RT-PCR. Dspp and enamelysin are differentiation markers specific for odontoblasts.

Primers for PPARγ, β-actin, Dspp, and enamelysin (matrix metalloproteinase (MMP) 20) shown in FIGS. 14D and 14G are shown in Table 3.

TABLE 3

|  | 5-Sequence-3' | Product size (bp) | Accession number |
|---|---|---|---|
| PPARγ | Forward: gctgtgcagg agatcacaga (SEQ ID NO: 5)<br>Reverse: gggctccata aagtcaccaa (SEQ ID NO: 6) | 225 | U63415 |
| β-actin | Forward: ggacttcgag caagagatgg (SEQ ID NO: 7)<br>Reverse: agcactgtgt tggcgtacag (SEQ ID NO: 8) | 234 | NM_001101 |
| Dspp | Forward: gaagatgctg gcctggataa (SEQ ID NO: 9)<br>Reverse: tcttctttcc catggtcctg (SEQ ID NO: 10) | 164 | NM_014208 |
| Enamelysin | Forward: ggtgagatgg ttgcaaga (SEQ ID NO: 11)<br>Reverse: ggaagaggcg ataattgg (SEQ ID NO: 12) | 163 | NM_004771 |

TABLE 2

|  | CD31⁻SP (%) | CD105⁺ (%) | total (%) |
|---|---|---|---|
| CD31 | 0.0 | 0.2 | 0.06 |
| CD146 | 0.0 | 2.0 | 40.58 |
| CD24 | 0.1 | 11.5 | 23.87 |
| CD34 | 0.01 | 0.0 | 0.01 |
| CD40 | 0.0 | 0.0 | 0.0 |
| CD44 | 92.5 | 98.9 | 91.6 |
| CD90 | 98.7 | 30.6 | 72.7 |
| CD105 | 21.2 | 92.0 | 4.4 |
| CD117 | 0.02 | 0.0 | 0.06 |
| CD133 | 0.01 | 0.0 | 0.5 |
| CD150 | 0.21 | 3.5 | 0.1 |
| CD271 | 0.03 | 2.9 | 0.01 |

As shown in Table 2, the human dental pulp tissue-derived CD105⁺ cells more highly expressed neural stem cell markers CD24 and CD271 and a more undifferentiated stem cell marker CD150 than human dental pulp tissue-derived CD31⁻/CD146⁻ SP cells and human total dental pulp cells. This suggests that the CD105⁺ cells are richer in neural stem cells and more undifferentiated stem cells than CD31⁻/CD146⁻ SP cells and human total dental pulp cells.

Next, to elucidate the characteristics of human dental pulp tissue-derived CD105⁺ cells, multipotency was examined.

As shown in FIG. 14A, the human dental pulp tissue derived CD105⁺ cells were induced to differentiate into blood vessels.

Moreover, as shown in FIG. 14B, the human dental pulp tissue-derived CD105⁺ cells were induced to differentiate into adipose tissue. On the other hand, as shown in FIG. 14C, the induction of differentiation into adipose tissue was not seen in the PBS control. FIG. 14D shows results of measurement by real-time RT-PCR. PPARγ is a differentiation marker specific for adipose cells.

Figure 15A:
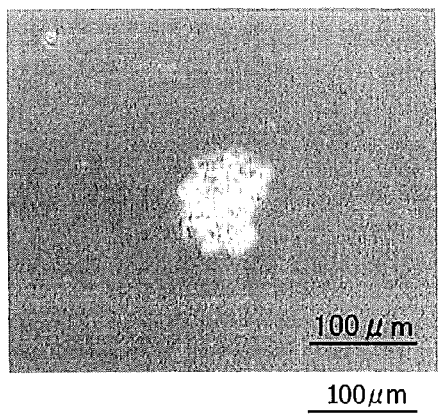
FIG. 15A shows the neurosphere formation of human dental pulp tissue-derived CD105$^+$ cells.
Figure 15B:
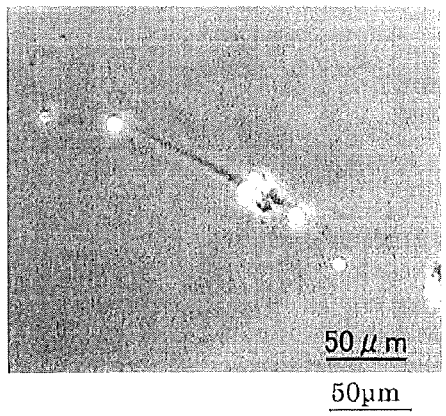
FIG. 15B shows the neural differentiation potency of human dental pulp tissue-derived CD105$^+$ cells.

Next, as shown in FIG. 15A, the human dental pulp tissue-derived CD105⁺ cells exhibited neurosphere formation. Moreover, as shown in FIG. 15B, the human dental pulp tissue-derived CD105⁺ cells had neural differentiation potency.

Figure 15C:
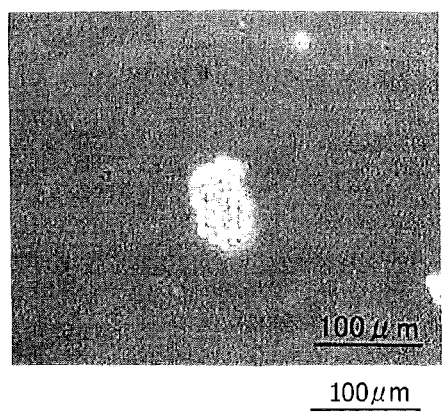
FIG. 15C shows the neurosphere formation of human dental pulp tissue-derived CD31$^-$/CD146$^-$ SP cells.
Figure 15D:
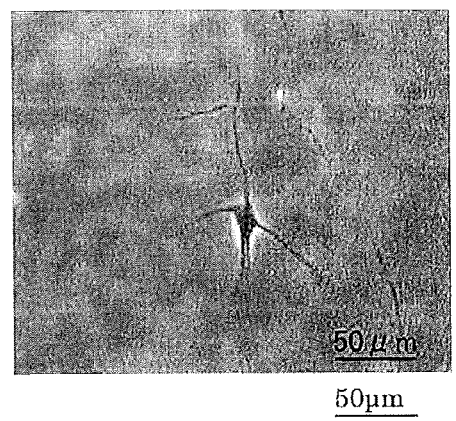
FIG. 15D shows the neural differentiation potency of human dental pulp tissue-derived CD31⁻/CD146⁻ SP cells.

Moreover, as shown in FIG. 15C, the human dental pulp tissue-derived CD31⁻/CD146⁻ SP cells exhibited neurosphere formation. Moreover, as shown in FIG. 15D, the human dental pulp tissue-derived CD31⁻/CD146⁻ SP cells had neural differentiation potency.

Next, human dental pulp tissue-derived CD105⁺ cells and human dental pulp tissue-derived CD31⁻/CD146⁻ SP cells were examined for their expression of neurotrophic factors and stem cell markers by real-time RT-PCR. The results are shown in Table 4 below.

TABLE 4

|  | CD31⁻/CD146⁻SP/<br>total pulp | CD105⁺/<br>total pulp |
|---|---|---|
| BDNF | 4.6 | 1.2 |
| NGF | 4.5 | 0.8 |
| GDNF | 0.4 | 4.1 |
| Neurotrophin 3 | 0.8 | 0.2 |
| VEGFA | 3.7 | 4.6 |
| Stat3 | 4.7 | 0.8 |
| Bmi1 | 2.4 | 0.6 |

Primers for BDNF, NGF, GDNF, Neurotrophin 3, VEGFA, Stat3, and Bmi1 are shown in Table 5.

TABLE 5

| | 5-Sequence-3' | Product size (bp) | Accession number |
|---|---|---|---|
| BDNF | Forward: aaacatccga ggacaaggtg (SEQ ID NO: 13)<br>Reverse: cgtgtacaag tctgcgtcct (SEQ ID NO: 14) | 202 | NM_170735 |
| NGF | Forward: atacaggcgg aaccacactc (SEQ ID NO: 15)<br>Reverse: gcctggggtc cacagtaat (SEQ ID NO: 16) | 181 | NM_002506 |
| GDNF | Forward: ttaggtactg cagcggctct (SEQ ID NO: 17)<br>Reverse: tccacaccTT ttagcggaat (SEQ ID NO: 18) | 203 | BC128108 |
| Neutrophine 3 | Forward: agactcgctc aattccctca (SEQ ID NO: 19)<br>Reverse: ggtgtccatt gcaatcactg (SEQ ID NO: 20) | 187 | BC107075 |
| VEGFA | Forward: ctacctccac catgccaagt (SEQ ID NO: 21)<br>Reverse: cacacaggat ggcttgaaga (SEQ ID NO: 22) | 187 | NM_001033756 |
| Stat3 | Forward: gtggtgacgg agaagcagca (SEQ ID NO: 23)<br>Reverse: ttctgcctgg tcactgactg (SEQ ID NO: 24) | 191 | NM_213662 |
| Bmi1 | Forward: atatttacgg tgcccagcag (SEQ ID NO: 25)<br>Reverse: gaagtggccc attccttctc (SEQ ID NO: 26) | 179 | CK_451985 |

The human dental pulp tissue-derived CD31⁻/CD146⁻ SP cells had the expression of brain-derived neurotrophic factor (BDNF) and nerve growth factor (NGF) mRNA 4 to 5 times higher than that of total dental pulp cells. The human dental pulp tissue-derived CD31⁻/CD146⁻ SP cells were confirmed to have the expression of BDNF about 4 times higher and the expression of NGF mRNA about 5.6 times higher than those of human dental pulp tissue-derived CD105⁺ cells. Both the cell fractions were confirmed to have the expression of VEGFA mRNA 4 to 5 times higher than that of total dental pulp cells.

On the other hand, the human dental pulp tissue-derived CD105⁺ cells were confirmed to have approximately 4-fold increase in the expression of glial cell-derived neurotrophic factor (GDNF) mRNA compared with that of total dental pulp cells. Moreover, the human dental pulp tissue-derived CD105⁺ cells were confirmed to have approximately 10.2-fold increase in the expression of glial cell-derived neurotrophic factor (GDNF) mRNA compared with that of human dental pulp tissue-derived CD31⁻/CD146⁻ SP cells.

Specifically, these results demonstrated that human dental pulp tissue-derived CD31⁻/CD146⁻ SP cells strongly express BDNF and NGF. Moreover, the results demonstrated that human dental pulp tissue-derived CD105⁺ cells strongly express GDNF mRNA.

The human dental pulp tissue-derived CD31⁻/CD146⁻ SP cells expressed the stem cell marker Stat3 mRNA about 5.8 times more strongly than human dental pulp tissue-derived CD105⁺ cells. The human dental pulp tissue-derived CD31⁻/CD146⁻ SP cells expressed the stem cell marker Bmi1 mRNA about 4 times more strongly than human dental pulp tissue-derived CD105⁺ cells.

These results suggest that the migration- and growth-promoting effects of human dental pulp tissue-derived CD31⁻/CD146⁻ SP cells are based mainly on BDNF and NGF and these effects of human dental pulp tissue-derived CD105⁺ cells are based mainly on GDNF.

Next, cultured neural progenitor cells (SHSY5Y human neuroblastomas) were used to examine culture supernatants of human dental pulp tissue-derived CD31⁻/CD146⁻ SP cells and human dental pulp tissue-derived CD105⁺ cells for their migratory effects, proliferative effects, and anti-apoptotic effects.

Figure 16:
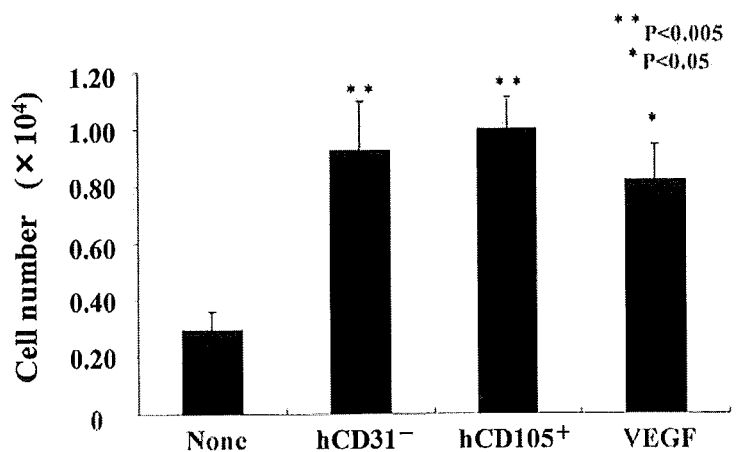
FIG. 16 illustrates the migration effects of culture supernatants of human dental pulp tissue-derived CD105⁺ cells and human dental pulp tissue-derived CD31⁻/CD146⁻ SP cells on neural progenitor cells.

FIG. 16 illustrates the enhanced migration by the conditioned medium of human dental pulp tissue-derived CD105⁺ cells and human dental pulp tissue-derived CD31⁻/CD146⁻ SP cells. As shown in FIG. 16, the conditioned medium of human dental pulp tissue-derived CD31⁻/CD146⁻ SP cells and human dental pulp tissue-derived CD105⁺ cells significantly promoted migration compared with the control.

Figure 17:
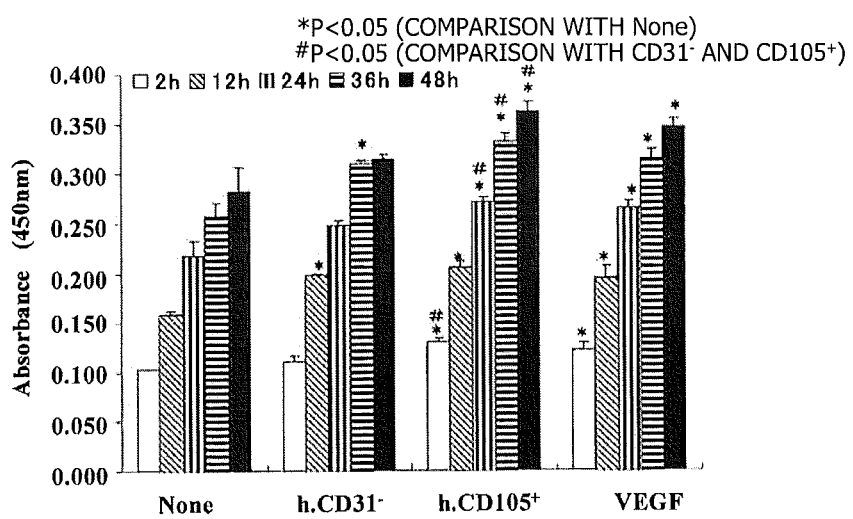
FIG. 17 illustrates the growth effects of culture supernatants of human dental pulp tissue-derived CD105⁺ cells and human dental pulp tissue-derived CD31⁻/CD146⁻ SP cells on neural progenitor cells.

FIG. 17 illustrates the enhanced proliferation of conditioned medium of human dental pulp tissue-derived CD105⁺ cells and human dental pulp tissue-derived CD31⁻/CD146⁻ SP cells. As shown in FIG. 17, the conditioned medium of human dental pulp tissue-derived CD31⁻/CD146⁻ SP cells and human dental pulp tissue-derived CD105⁺ cells significantly promoted proliferation compared with the control. Moreover, the conditioned medium of human dental pulp tissue-derived CD105⁺ cells more highly promoted proliferation with significant difference than the conditioned medium of human dental pulp tissue-derived CD31⁻/CD146⁻ SP cells after 24 hours. The significant difference between them was more marked after 48 hours.

Figure 18:
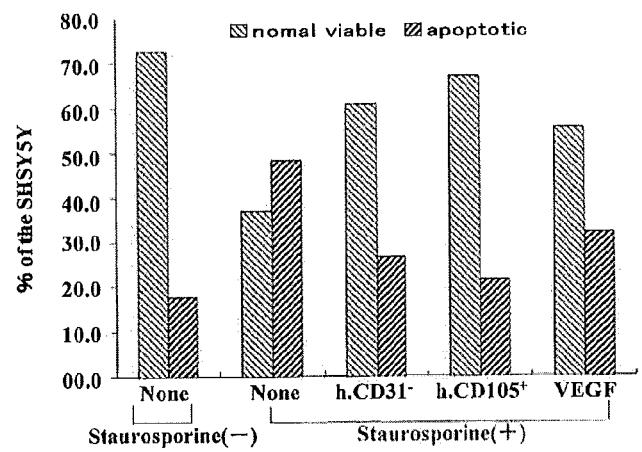
FIG. 18 shows the apoptosis inhibitory effects of human dental pulp tissue-derived CD105⁺ cells and human dental pulp tissue-derived CD31⁻/CD146⁻ SP cells on neural progenitor cells.

FIG. 18 shows the anti-apoptotic effects of human dental pulp tissue-derived CD105⁺ cells and human dental pulp tissue-derived CD31⁻/CD146⁻ SP cells. As shown in FIG. 18, the conditioned medium of human dental pulp tissue-derived CD31⁻/CD146⁻ SP cells and human dental pulp tissue-derived CD105⁺ cells significantly inhibited apoptosis compared with the control. Moreover, the conditioned medium of human dental pulp tissue-derived CD105⁺ cells more markedly inhibited apoptosis than the conditioned medium of human dental pulp tissue-derived CD31⁻/CD146⁻ SP cells.

Next, human dental pulp tissue-derived CD31⁻/CD146⁻ SP cells and human dental pulp tissue-derived CD105⁺ cells were separately transplanted into the corpus striatum in the brain tissues after cerebral infarction, and the motor disability scores were determined over time to examine the recovery effect of cell transplantation on motor function.

Models of cerebral infarction were prepared using SD rats in the same way as in Example 1. Human dental pulp tissue-derived CD31⁻/CD146⁻ SP cells and CD105⁺ cells were fluorescently labeled with DiI and then transplanted into the corpus striatum in brain tissues 24 hours after cerebral infarction.

A PBS-injected control was used. Then, 21 days after cerebral infraction, perfusion fixation was performed, and frozen sections were prepared according to a routine method and immunostained with a neural progenitor cell marker DCX and a neural marker NeuN. Furthermore, after cell transplantation, the motor disability scores were determined over time to examine the recovery effect of cell transplantation on motor sensation and function.

Figure 19:
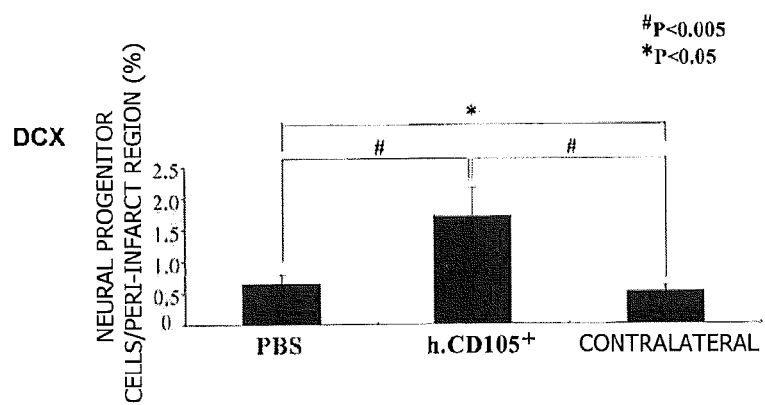
FIG. 19 shows results of statistically analyzing the density of DCX-immunostained neural progenitor cells in a peri-infarct area of the brain on day 21 from the cell transplantation of human dental pulp tissue-derived CD105⁺ cells into the corpus striatum in the brain tissues 24 hours after cerebral infarction.

FIG. 19 shows results of statistically analyzing the density of DCX-immunostained neural progenitor cells on day 21 from the cell transplantation of human dental pulp tissue-derived CD105$^+$ cells into the corpus striatum in the brain tissues after cerebral infarction. As shown in FIG. 19, in the transplantation of human dental pulp tissue-derived CD105$^+$ cells there was a 3 times increase in the neural progenitor cells at the periphery of the cerebral infarction region.

Figure 20:
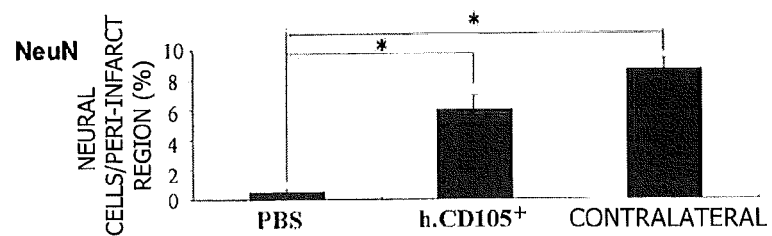
FIG. 20 shows results of statistically analyzing the density of NeuN-immunofluorescently stained neural cells in a peri-infarct area of the brain on day 21 from the cell transplantation of human dental pulp tissue-derived CD105⁺ cells into the corpus striatum in the brain tissues 24 hours after cerebral infarction.

FIG. 20 shows results of statistical analysis of the density of NeuN-immunofluorescently stained neural cells on day 21 in the cell transplantation of human dental pulp tissue-derived CD105$^+$ cells into the corpus striatum in the brain tissues after cerebral infarction. As shown in FIG. 20, the neural cells were significantly increased in the peri-infarct region of the brain compared with the PBS-injected control, although the neural cells exhibited a disturbed nerve tract compared with the corresponding area of a normal brain region located on the contralateral side.

Figure 21:
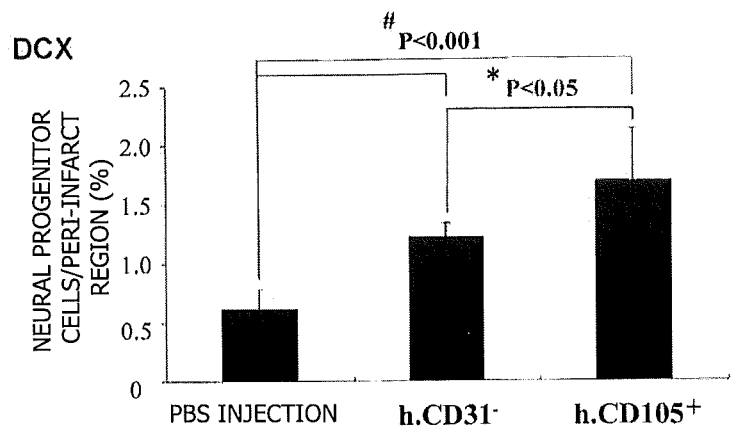
FIG. 21 shows results of statistically analyzing the density of DCX-immunostained neural progenitor cells in a peri-infarct area of the brain on day 21 from the cell transplantation of human dental pulp tissue-derived CD105⁺ cells and human dental pulp tissue-derived CD31⁻/CD146⁻ SP cells into the corpus striatum in the brain tissues 24 hours after cerebral infarction.

FIG. 21 shows results of statistical analysis of the density of DCX-immunostained neural progenitor cells on day 21 in human dental pulp tissue-derived CD105$^+$ cell transplantation compared with that in human dental pulp tissue-derived CD31$^-$/CD146$^-$ SP cell transplantation into the corpus striatum in the brain tissues of different SD rats with cerebral infarction. As shown in FIG. 21, the human dental pulp tissue-derived CD105$^+$ cells had the more marked ability to promote proliferation of neural progenitor cells than that of human dental pulp tissue-derived CD31$^-$/CD146$^-$ SP cells.

Figure 22:
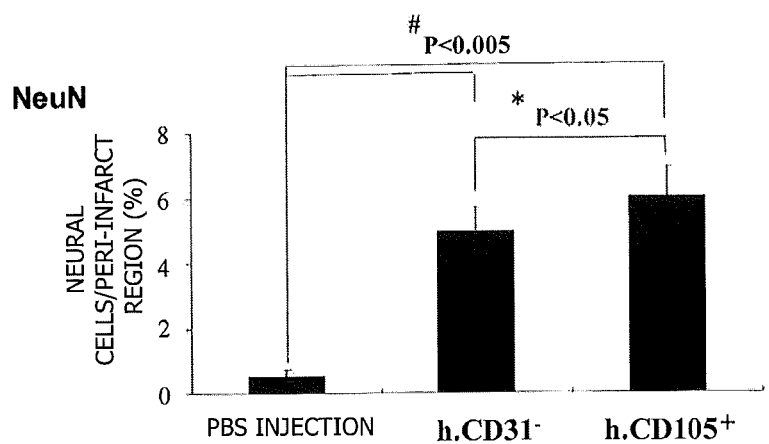
FIG. 22 shows results of statistically analyzing the density of NeuN-immunostained neural cells in a peri-infarct area of the brain on day 21 from the cell transplantation of human dental pulp tissue-derived CD105⁺ cells and human dental pulp tissue-derived CD31⁻/CD146⁻ SP cells into the corpus striatum in the brain tissues 24 hours after cerebral infarction.

FIG. 22 shows results of statistical analysis of the density of NeuN-immunostained neural cells on day 21 in human dental pulp tissue-derived CD105$^+$ cell transplantation with that in human dental pulp tissue-derived CD31$^-$/CD146$^-$ SP cell transplantation into the corpus striatum in the brain tissues of different SD rats with cerebral infarction. As shown in FIG. 22, the human dental pulp tissue-derived CD105$^+$ cells had the more marked ability to promote the differentiation of neural cells than that of human dental pulp tissue-derived CD31$^-$/CD146$^-$ SP cells.

These results demonstrated that human dental pulp tissue-derived transplanted cells do not directly differentiate into neural progenitor cells or neural cells and indirectly participate in the promotion of differentiation, as with porcine dental pulp tissue-derived transplanted cells.

Figure 23:
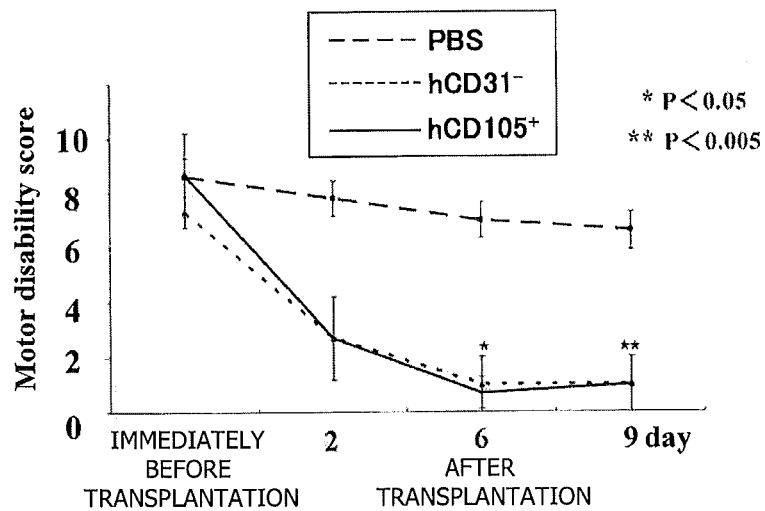
FIG. 23 shows results of determining over time and statistically analyzing the motor disability scores of rats with cerebral infarction transplanted with human dental pulp tissue-derived CD105⁺ cells and human dental pulp tissue-derived CD31⁻/CD146⁻ SP cells.

FIG. 23 shows results of statistical analysis of the motor disability scores of different SD rats with cerebral infarction in human dental pulp tissue-derived CD105$^+$ cell transplantation and human dental pulp tissue-derived CD31$^-$/CD146$^-$ SP cells compared with PBS control transplantation. The number of days is counted from cell transplantation. As shown in FIG. 23, when the motor disability scores were determined over time, significant recovery from motor disability were demonstrated both in the human dental pulp tissue-derived CD31$^-$/CD146$^-$ SP cell transplantation and the human dental pulp tissue-derived CD105$^+$ cell transplantation compared with the PBS-injected control.

As shown in these Examples, the dental pulp tissue-derived CD105$^+$ cells and the dental pulp tissue-derived CD31$^-$/CD146$^-$ SP cells have significant effects on cell migration, proliferation, and anti-apoptosis, and also have significant effects on enhanced proliferation of neural progenitor cells and neural cell differentiation.

Moreover, as shown in these Examples, the dental pulp tissue-derived CD105$^+$ cells have significantly higher effects on proliferation and anti-apoptosis compared with the dental pulp tissue-derived CD31$^-$/CD146$^-$ SP cells. The marked superiority of the dental pulp tissue-derived CD105$^+$ cells over the dental pulp tissue-derived CD31$^-$/CD146$^-$ SP cells could not have been predicted and has been revealed for the first time by the experiments of the present inventors.

Furthermore, although flow cytometry is used for fractionating the dental pulp tissue-derived CD31$^-$/CD146$^-$ SP cells, flow cytometry may cause contamination with cells derived from other individuals. Therefore, fractionation using flow cytometry cannot be used clinically from the viewpoint of safety. On the other hand, the dental pulp tissue-derived CD105$^+$ cells can be fractionated by, for example, an immunological magnetic bead method, without particular limitations. The immunological magnetic bead method involves reacting samples with immunological magnetic beads (magnetic bead-conjugated antibodies against cell surface antigens) placed in a tube and adsorbing the samples onto the column for separation. This method is free from the risk of contamination. Therefore, the material for treatment of cerebral infarction comprising dental pulp tissue-derived CD105$^+$ cells has the great advantage that it can be used clinically on the spot and can immediately provide therapeutic means appropriate for cerebral angiopathy.

A material for treatment of cerebral infarction according to the present invention is effective to enhance proliferation of neural progenitor cells and also effective to promote neural cell differentiation. Moreover, the material for treatment of cerebral infarction according to the present invention can be used clinically on the spot and can immediately provide therapeutic means appropriate for cerebral angiopathy.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

That which is claimed:

1. A brain tissue regeneration method comprising injecting at least one of: dental pulp cells comprising CD105-positive cells fractionated from human dental pulp cell populations; and culture supernatants comprising a secretory protein from CD105-positive cells fractionated from human dental pulp cell populations, into a target animal undergoing treatment for improving brain function, thereby regenerating the central nervous tissue of the brain to recover brain function.

2. The brain tissue regeneration method according to claim 1, wherein the CD105-positive cells express a factor comprising at least one of a cell migration factor, a cell growth factor, an angiogenic factor, and a neurotrophic factor in a peri-infarct region of the brain.

3. The brain tissue regeneration method according to claim 2, wherein the cell migration factor is at least one of SDF1, GCSF, MMP3, Slit, and GMCSF.

4. The brain tissue regeneration method according to claim 2, wherein the neurotrophic factor is at least one of VEGF, NGF, GDNF, BDNF, LIF, MYC, Neurotrophine 3, TP53, and BAX.

5. The brain tissue regeneration method according to claim 2, wherein the cell growth factor is at least one of bFGF and PDGF.

6. The brain tissue regeneration method according to claim 2, wherein the angiogenic factor is at least one of CXCL1, CXCL2, CXCL3, CXCL5, CXCL10, ANPEP, NRP1, TGFβ, ECGF1, ID1, and CSF3.

7. The brain tissue regeneration method according to claim 1, wherein the CD105-positive cells are injected at a concentration of $1\times10^5$ cells/µl to $1\times10^7$ cells/µl.

8. The brain tissue regeneration method according to claim 1, wherein the CD105-positive cells are derived from a permanent tooth or a deciduous tooth.

9. The brain tissue regeneration method according to claim 1, wherein the CD105-positive cells are cryopreserved cells.

10. The brain tissue regeneration method according to claim 1, wherein the CD105-positive cells are autologous cells.

11. The brain tissue regeneration method according to claim 1, wherein the CD105-positive cells are allogenic cells or xenogenic cells.

12. The brain tissue regeneration method according to claim 1, wherein the injecting step is carried out after a cerebral infarction to restore a cerebral infarction region.

13. The method according to claim 1, wherein the method comprises injecting at least one of: dental pulp cells consisting essentially of CD105-positive cells fractionated from human dental pulp cell populations; and culture supernatants comprising a secretory protein from CD105-positive cells fractioned from human dental pulp cell populations.

14. A brain tissue regeneration method comprising injecting at least one of: dental pulp cells comprising a CD105-positive cells fractionated from human dental pulp cell populations; and culture supernatants comprising a secretory protein from CD105-positive cells fractionated from human dental pulp cell populations, into the brain striatum after cerebral infarction, thereby regenerating the central nervous tissue of the brain to recover brain function.

15. The method according to claim 14, wherein the method comprises injecting at least one of: dental pulp cells consisting essentially of CD105-positive cells fractionated from human dental pulp cell populations; and culture supernatants comprising a secretory protein from CD105-positive cells fractionated from human dental pulp cell populations.

* * * * *

SEQUENCE LISTING

```
<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: RT-PCR primer

<400> SEQUENCE: 1
ctggggccta acgttctcac                                                   20
```

-continued

<210> SEQ ID NO 2
<211> LENGTH: 20
<212> TYPE: DNA
<213> ORGANISM: Artificial Sequence
<220> FEATURE:
<223> OTHER INFORMATION: RT-PCR primer

<400> SEQUENCE: 2
gtcctttctt ccccgatgtt            20

<210> SEQ ID NO 3
<211> LENGTH: 20
<212> TYPE: DNA
<213> ORGANISM: Artificial Sequence
<220> FEATURE:
<223> OTHER INFORMATION: RT-PCR primer

<400> SEQUENCE: 3
atggcagaag gagaccagaa            20

<210> SEQ ID NO 4
<211> LENGTH: 20
<212> TYPE: DNA
<213> ORGANISM: Artificial Sequence
<220> FEATURE:
<223> OTHER INFORMATION: RT-PCR primer

<400> SEQUENCE: 4
atggcgatgt tgaactcctc            20

<210> SEQ ID NO 5
<211> LENGTH: 20
<212> TYPE: DNA
<213> ORGANISM: Artificial Sequence
<220> FEATURE:
<223> OTHER INFORMATION: RT-PCR primer

<400> SEQUENCE: 5
gctgtgcagg agatcacaga            20

<210> SEQ ID NO 6
<211> LENGTH: 20
<212> TYPE: DNA
<213> ORGANISM: Artificial Sequence
<220> FEATURE:
<223> OTHER INFORMATION: RT-PCR primer

<400> SEQUENCE: 6
gggctccata aagtcaccaa            20

<210> SEQ ID NO 7
<211> LENGTH: 20
<212> TYPE: DNA
<213> ORGANISM: Artificial Sequence
<220> FEATURE:
<223> OTHER INFORMATION: RT-PCR primer

<400> SEQUENCE: 7
ggacttcgag caagagatgg            20

<210> SEQ ID NO 8
<211> LENGTH: 20
<212> TYPE: DNA
<213> ORGANISM: Artificial Sequence
<220> FEATURE:
<223> OTHER INFORMATION: RT-PCR primer

```
<400> SEQUENCE: 8
agcactgtgt tggcgtacag                                              20

<210> SEQ ID NO 9
<211> LENGTH: 20
<212> TYPE: DNA
<213> ORGANISM: Artificial Sequence
<220> FEATURE:
<223> OTHER INFORMATION: RT-PCR primer

<400> SEQUENCE: 9
gaagatgctg gcctggataa                                              20

<210> SEQ ID NO 10
<211> LENGTH: 20
<212> TYPE: DNA
<213> ORGANISM: Artificial Sequence
<220> FEATURE:
<223> OTHER INFORMATION: RT-PCR primer

<400> SEQUENCE: 10
tcttctttcc catggtcctg                                              20

<210> SEQ ID NO 11
<211> LENGTH: 18
<212> TYPE: DNA
<213> ORGANISM: Artificial Sequence
<220> FEATURE:
<223> OTHER INFORMATION: RT-PCR primer

<400> SEQUENCE: 11
ggtgagatgg ttgcaaga                                                18

<210> SEQ ID NO 12
<211> LENGTH: 18
<212> TYPE: DNA
<213> ORGANISM: Artificial Sequence
<220> FEATURE:
<223> OTHER INFORMATION: RT-PCR primer

<400> SEQUENCE: 12
ggaagaggcg ataattgg                                                18

<210> SEQ ID NO 13
<211> LENGTH: 20
<212> TYPE: DNA
<213> ORGANISM: Artificial Sequence
<220> FEATURE:
<223> OTHER INFORMATION: RT-PCR primer

<400> SEQUENCE: 13
aaacatccga ggacaaggtg                                              20

<210> SEQ ID NO 14
<211> LENGTH: 20
<212> TYPE: DNA
<213> ORGANISM: Artificial Sequence
<220> FEATURE:
<223> OTHER INFORMATION: RT-PCR primer

<400> SEQUENCE: 14
cgtgtacaag tctgcgtcct                                              20
```

<210> SEQ ID NO 15
<211> LENGTH: 20
<212> TYPE: DNA
<213> ORGANISM: Artificial Sequence
<220> FEATURE:
<223> OTHER INFORMATION: RT-PCR primer

<400> SEQUENCE: 15
atacaggcgg aaccacactc                                                 20

<210> SEQ ID NO 16
<211> LENGTH: 19
<212> TYPE: DNA
<213> ORGANISM: Artificial Sequence
<220> FEATURE:
<223> OTHER INFORMATION: RT-PCR primer

<400> SEQUENCE: 16
gcctggggtc cacagtaat                                                  19

<210> SEQ ID NO 17
<211> LENGTH: 20
<212> TYPE: DNA
<213> ORGANISM: Artificial Sequence
<220> FEATURE:
<223> OTHER INFORMATION: RT-PCR primer

<400> SEQUENCE: 17
ttaggtactg cagcggctct                                                 20

<210> SEQ ID NO 18
<211> LENGTH: 20
<212> TYPE: DNA
<213> ORGANISM: Artificial Sequence
<220> FEATURE:
<223> OTHER INFORMATION: RT-PCR primer

<400> SEQUENCE: 18 tccacaccctt ttagcggaat                                                20

<210> SEQ ID NO 19
<211> LENGTH: 20
<212> TYPE: DNA
<213> ORGANISM: Artificial Sequence
<220> FEATURE:
<223> OTHER INFORMATION: RT-PCR primer

<400> SEQUENCE: 19
agactcgctc aattccctca                                                 20

<210> SEQ ID NO 20
<211> LENGTH: 20
<212> TYPE: DNA
<213> ORGANISM: Artificial Sequence
<220> FEATURE:
<223> OTHER INFORMATION: RT-PCR primer

<400> SEQUENCE: 20
ggtgtccatt gcaatcactg                                                 20

<210> SEQ ID NO 21
<211> LENGTH: 20
<212> TYPE: DNA
<213> ORGANISM: Artificial Sequence
<220> FEATURE:
<223> OTHER INFORMATION: RT-PCR primer

```
<400> SEQUENCE: 21
ctacctccac catgccaagt                                               20

<210> SEQ ID NO 22
<211> LENGTH: 20
<212> TYPE: DNA
<213> ORGANISM: Artificial Sequence
<220> FEATURE:
<223> OTHER INFORMATION: RT-PCR primer

<400> SEQUENCE: 22
cacacaggat ggcttgaaga                                               20

<210> SEQ ID NO 23
<211> LENGTH: 20
<212> TYPE: DNA
<213> ORGANISM: Artificial Sequence
<220> FEATURE:
<223> OTHER INFORMATION: RT-PCR primer

<400> SEQUENCE: 23
gtggtgacgg agaagcagca                                               20

<210> SEQ ID NO 24
<211> LENGTH: 20
<212> TYPE: DNA
<213> ORGANISM: Artificial Sequence
<220> FEATURE:
<223> OTHER INFORMATION: RT-PCR primer

<400> SEQUENCE: 24
ttctgcctgg tcactgactg                                               20

<210> SEQ ID NO 25
<211> LENGTH: 20
<212> TYPE: DNA
<213> ORGANISM: Artificial Sequence
<220> FEATURE:
<223> OTHER INFORMATION: RT-PCR primer

<400> SEQUENCE: 25
atatttacgg tgcccagcag                                               20

<210> SEQ ID NO 26
<211> LENGTH: 20
<212> TYPE: DNA
<213> ORGANISM: Artificial Sequence
<220> FEATURE:
<223> OTHER INFORMATION: RT-PCR primer

<400> SEQUENCE: 26
gaagtggccc attccttctc                                               20
```